US011484359B2

(12) United States Patent
Berman et al.

(10) Patent No.: US 11,484,359 B2
(45) Date of Patent: Nov. 1, 2022

(54) METHOD AND SYSTEM FOR GAP DETECTION IN ABLATION LINES

(71) Applicant: Biosense Webster (Israel) Ltd., Yokneam (IL)

(72) Inventors: Dror Berman, Haifa (IL); Assaf Pressman, Pardes Hanna-Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 349 days.

(21) Appl. No.: 15/799,254

(22) Filed: Oct. 31, 2017

(65) Prior Publication Data

US 2019/0125438 A1    May 2, 2019

(51) Int. Cl.
*A61B 18/14*    (2006.01)
*A61B 18/12*    (2006.01)
(Continued)

(52) U.S. Cl.
CPC ...... *A61B 18/1492* (2013.01); *A61B 18/1233* (2013.01); *A61B 5/283* (2021.01);
(Continued)

(58) Field of Classification Search
CPC . A61B 5/04012; A61B 5/0402; A61B 5/0432; A61B 2018/00345;
(Continued)

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| EP | 3181078 A1 | 6/2017 |
| JP | 2007-244857 A | 9/2007 |

(Continued)

OTHER PUBLICATIONS

Extended European Search Report dated Jan. 17, 2019 for the European Patent Application No. 18203277.1.
(Continued)

*Primary Examiner* — Ronald Hupczey, Jr.
(74) *Attorney, Agent, or Firm* — Volpe Koenig

(57) ABSTRACT

Described herein is a method and system for gap detection in ablation lines. Microelectrodes are implemented at a distal tip of a catheter to provide localized gap detection along an ablation line. A pacing protocol is used to sequence through each of the microelectrode pairs for a tissue location. If living tissue is present, the pacing signal travels through the living tissue to pulse the heart. An operator will see a capture signal and know that there is a gap in the ablation line. The ablation electrode is then used to ablate the tissue in the gap. Pacing and ablation are therefore performed at the same place without the need to switch between instruments and/or catheters. In an implementation, a force sensor can automate the pacing protocol by determining which microelectrode pair is contacting the tissue. Moreover, signaling between microelectrode pairs can determine contact between the catheter and the tissue.

20 Claims, 5 Drawing Sheets

(51) Int. Cl.

| | | |
|---|---|---|
| *A61B 18/00* | (2006.01) | |
| *A61N 1/37* | (2006.01) | |
| *A61N 1/05* | (2006.01) | |
| *A61B 5/00* | (2006.01) | |
| *A61B 90/00* | (2016.01) | |
| *A61B 5/283* | (2021.01) | |

(52) U.S. Cl.
CPC ... *A61B 5/6885* (2013.01); *A61B 2018/00357* (2013.01); *A61B 2018/00577* (2013.01); *A61B 2018/00654* (2013.01); *A61B 2018/00702* (2013.01); *A61B 2018/00821* (2013.01); *A61B 2018/00839* (2013.01); *A61B 2018/00875* (2013.01); *A61B 2018/00904* (2013.01); *A61B 2018/126* (2013.01); *A61B 2018/1467* (2013.01); *A61B 2090/065* (2016.02); *A61N 1/056* (2013.01); *A61N 1/371* (2013.01)

(58) Field of Classification Search
CPC ........... A61B 2018/00363; A61B 2018/00636; A61B 2018/00791; A61B 2018/00821; A61B 2018/00904; A61B 18/1492
See application file for complete search history.

(56) References Cited

U.S. PATENT DOCUMENTS

| | | | |
|---|---|---|---|
| 5,545,161 A * | 8/1996 | Imran | ................ A61B 18/1492 606/41 |
| 5,558,091 A | 9/1996 | Acker et al. | |
| 5,836,874 A * | 11/1998 | Swanson | ............ A61B 18/1492 600/374 |
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,264,653 B1 * | 7/2001 | Falwell | .............. A61B 18/1492 606/34 |
| 6,266,551 B1 | 7/2001 | Osadchy et al. | |
| 6,456,864 B1 | 9/2002 | Swanson et al. | |
| 6,690,963 B2 | 2/2004 | Ben-Haim et al. | |
| 6,788,967 B2 | 9/2004 | Ben-Haim et al. | |
| 7,542,807 B2 * | 6/2009 | Bertolero | ................. A61N 1/05 607/119 |
| 10,383,543 B2 | 8/2019 | Bonyak et al. | |
| 2004/0092806 A1 | 5/2004 | Sagon et al. | |
| 2007/0198007 A1 | 8/2007 | Govari et al. | |
| 2008/0243214 A1 | 10/2008 | Koblish | |
| 2009/0093806 A1 | 4/2009 | Govari et al. | |
| 2009/0138007 A1 | 5/2009 | Govari et al. | |
| 2013/0190747 A1 * | 7/2013 | Koblish | ................. A61B 5/287 606/33 |
| 2013/0253504 A1 * | 9/2013 | Fang | ................. A61B 18/1492 606/41 |
| 2015/0066021 A1 * | 3/2015 | Gliner | ................. A61B 5/6885 606/41 |
| 2015/0374252 A1 | 12/2015 | de la Rama et al. | |
| 2016/0113582 A1 | 4/2016 | Altmann et al. | |
| 2017/0042615 A1 | 2/2017 | Salahieh et al. | |

FOREIGN PATENT DOCUMENTS

| | | |
|---|---|---|
| JP | 2015-506234 A | 3/2015 |
| JP | 2017-086913 A | 5/2017 |
| WO | 2013/106557 A1 | 7/2013 |

OTHER PUBLICATIONS

Japanese Office Action dated Aug. 2, 2022 for Japanese Patent Application No. 2018-203572.

* cited by examiner

METHOD AND SYSTEM FOR GAP DETECTION IN ABLATION LINES

SUMMARY

Described herein is a method and system for gap detection in ablation lines. A set of microelectrodes is implemented at a distal tip of a catheter in addition to the standard sensors and electrodes present in the catheter. These microelectrodes provide localized gap detection along an ablation line. The system uses a pacing protocol to sequence through each pairing of microelectrodes for a given tissue location. A pacing signal is applied to the tissue location. If living tissue is present, the pacing signal travels through the living tissue to pulse the heart. An operator will see a capture signal from the heart and know that there is a gap in the ablation line. The ablation electrode can then be used to ablate the tissue in the detected gap. Pacing and ablation are therefore performed at the same place without the need to switch between instruments and/or catheters. In an implementation, a force sensor can be used to automate the pacing protocol by determining which pair of electrodes is in contact with the tissue. In an implementation, signaling between a pair of microelectrodes can be used to determine if the catheter is in touch with the tissue. The presence of a signal indicating that the catheter is in touch with the tissue.

BRIEF DESCRIPTION OF THE DRAWINGS

A more detailed understanding may be had from the following description, given by way of example in conjunction with the accompanying drawings wherein.

DETAILED DESCRIPTION

Figure 1:
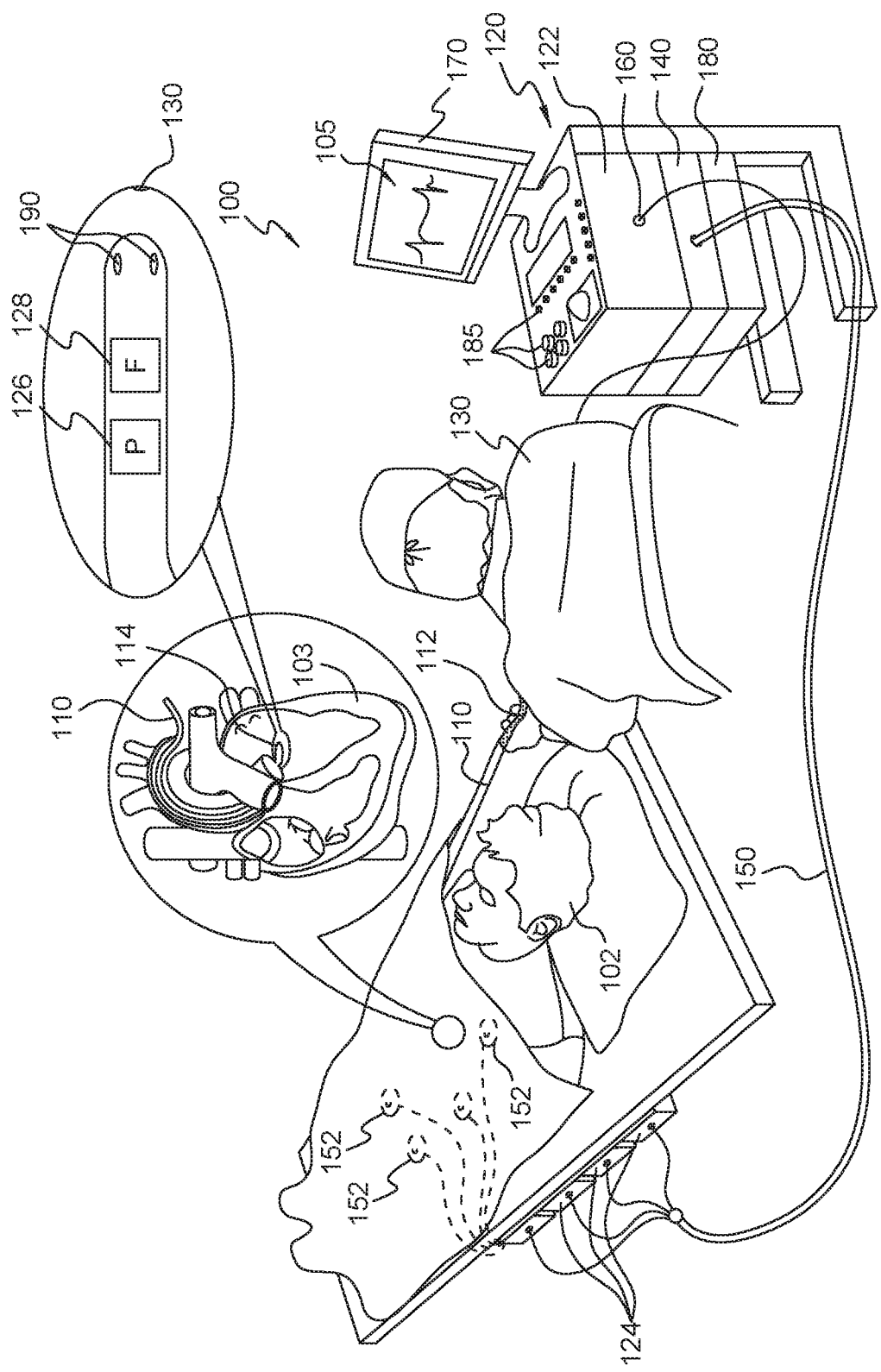
FIG. 1 is a high level schematic, pictorial illustration of a medical system in accordance with certain implementations.

Documents incorporated by reference in the present patent application may include terms that are defined in a manner that conflict with the definitions made explicitly or implicitly in the present specification. In the event of any conflicts, the definitions in the present specification should be considered to be controlling.

Cardiac ablation is a medical procedure performed by electrophysiologists that may be used to correct heart rhythm defects, known as arrhythmias, by creating lesions to destroy tissue in the heart that contributes to the rhythm defects. These lesions may also be referred to as ablation lines. An example arrhythmia that can be treated using cardiac ablation is atrial fibrillation (AF), which is an abnormal heart rhythm that originates in the atria of the heart. Goals of cardiac ablation are to remove the arrhythmia to return the patient's heart to a normal heart rhythm or reduce the frequency of arrhythmia and the severity of symptoms in the patient.

Cardiac ablation may employ long, flexible catheters (endoscope) that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. These lesions, also called transmural lesions, are scar tissue that penetrates the heart tissue and keeps errant electrical signals from being transmitted.

Physicians performing cardiac ablation procedures face a significant problem when they cannot guarantee or know for certainty that there is surface contact between the catheter, namely the ablation electrodes, and the tissue (i.e., the ablation target). As a result, performance of the cardiac ablation procedure might result in tissue that was not ablated as required and the ablation procedure is not successfully completed, (i.e., the arrhythmia may continue and the irregular heartbeats may continue). These non-ablated areas in the ablation lesion or line (hereinafter ablation line) are referred to as gaps. Therefore, physicians need an improved device to confirm that there are no gaps in the ablation line.

Described herein is a method and system for gap detection in ablation lines. In general, a catheter is equipped with microelectrodes to detect gaps in an ablation line. The microelectrodes provide localized gap detection along the ablation line. A pacing protocol is used to sequence through each microelectrode pair for a given tissue location. If the ablation line has no gaps, then there will only be scar tissue and scar tissue does not result in any return signals. If living tissue is present, the pacing signal travels through the living tissue to pulse the heart. An operator will see a capture signal from the heart on a sensor and know that there is a gap in the ablation line. In an implementation, the system can determine gaps based on the capture signal. The ablation electrode is then used to ablate the tissue in the detected gap. The system and/or device combines pacing and capture techniques, where the pacing and capture are testing methods, with an ablation procedure, which is a treatment method. Pacing/capturing and ablation are therefore performed at the same place without the need to switch between instruments and/or catheters.

In an implementation, a force sensor can be used to automate the pacing protocol by determining which pair(s) of electrodes is in contact with the tissue. In an implementation, signaling between a pair of microelectrodes can be used to determine if the catheter is in touch with the tissue. The presence of a signal indicating that the catheter is in touch with the tissue.

FIG. 1 is an illustration of an example medical system 100 that is used to generate and display information during a medical procedure and to control the deployment of various catheters within a subject. Example system 100 includes a catheter 110, such as an intracardiac catheter, a console 120 and an associated catheter control unit 112. As described herein, it will be understood that catheter 110 is used for diagnostic or therapeutic treatment, such as for example, mapping electrical potentials in a heart 103 of a patient 102 or performing an ablation procedure. Alternatively, catheter 110 can be used, mutatis mutandis, for other therapeutic and/or diagnostic purposes in heart 103, lungs, or in other body organs and ear, nose, and throat (ENT) procedures.

An operator 130 can, for example, insert catheter 110 into the vascular system of patient 102 using catheter control unit 112 so that a distal end 114 of catheter 110 enters a chamber of the patient's heart 103. Console 120 can use magnetic position sensing to determine position coordinates of distal end 114 inside heart 103. To determine the position coordinates, a driver circuit 122 in console 120 may drive field generators 124 to generate magnetic fields within the body of patient 102. Field generators 124 can include coils that may be placed below the torso of the patient 103 at known positions external to patient 103. These coils may generate magnetic fields in a predefined working volume that contains heart 103.

A location sensor 126 within distal end 114 of catheter 110 can generate electrical signals in response to these magnetic fields. Processing device(s) 140 can process these signals in order to determine the position coordinates of distal end 114, including both location and orientation coordinates. Known methods of position sensing described hereinabove are implemented in the CARTO™ mapping system produced by Biosense Webster Inc., of Diamond Bar, Calif., and is described in detail in the patents and the patent applications cited herein.

Location sensor 126 is configured to transmit a signal to console 120 that is indicative of the location coordinates of distal end 114. Location sensor 126 can include one or more miniature coils, and typically can include multiple coils oriented along different axes. Alternatively, location sensor 126 can comprise either another type of magnetic sensor or position transducers of other types, such as impedance-based or ultrasonic location sensors.

Catheter 110 can also include a force sensor 128 contained within distal end 114. Force sensor 128 can measure a force applied by distal end 114 to the endocardial tissue of heart 103 and generate a signal that is sent to console 120. Force sensor 128 can include a magnetic field transmitter and a receiver connected by a spring in distal end 114, and can generate an indication of the force based on measuring a deflection of the spring. Further functional details of the catheter and force sensor are described in U.S. Patent Application Publications 2009/0093806 and 2009/0138007, and are incorporated herein by reference as if fully set forth. Alternatively, distal end 114 can include another type of force sensor that can use, for example, fiber optics or impedance measurements.

Catheter 110 can include an electrode 130 coupled to distal end 114 and configured to function as an impedance-based position transducer. Additionally or alternatively, electrode 130 can be configured to measure a certain physiological property, for example the local surface electrical potential of the cardiac tissue at one or more of the multiple locations. Electrode 130 can be configured to apply radio frequency (RF) energy to ablate endocardial tissue in heart 103.

In a catheter 110 where electrode 130 is configured as an ablation electrode, catheter 110 can include microelectrodes 190 at distal end 114. Microelectrodes 190 are configured to detect a gap in the ablation line as described herein. Microelectrodes 190, as implied by the name, are smaller than standard, larger sized electrodes, such as for example, electrode 130, and are described herein below with respect to FIG. 3. Microelectrodes 190 can provide greater spatial resolution in detecting more subtle electrical activity of heart tissue in diagnosing arrhythmias.

Although example medical system 100 can be configured to measure the position of distal end 114 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558, 091, 6,172,499, and 6,177,792, and are incorporated herein by reference as if fully set forth. Impedance-based position tracking techniques are described, for example, in U.S. Pat. Nos. 5,983,126, 6,456,864 and 5,944,022, and are incorporated herein by reference as if fully set forth.

Processing device(s) 140 can be a general-purpose computer, with a suitable front end and interface circuits for receiving signals from catheter 110 and controlling the other components of console 120. Processing device(s) 140 can be programmed, using software, to carry out the functions that are described herein. The software can be downloaded to console 120 in electronic form, over a network, for example, or it can be provided on non-transitory tangible media, such as optical, magnetic or electronic memory media. Alternatively, some or all of the functions of processing device(s) 140 can be performed by dedicated or programmable digital hardware components.

Figure 1A:
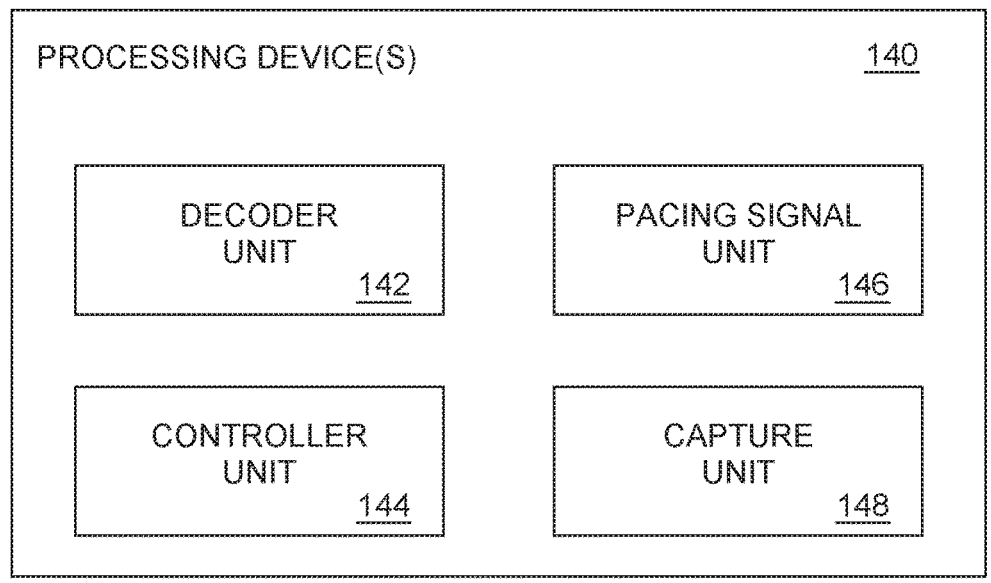
FIG. 1A is a high level block diagram of a medical system in accordance with certain implementations.

Referring now also to FIG. 1A, processing device(s) 140 may implement specific functions, which may be represented (e.g., illustratively or physically) as separate units within processing device(s) 140. For example, processing device(s) 140 may include a decoder unit 142 (e.g., implemented in hardware as a processing circuit and/or software as a software module) that may be configured to receive signals from sensors in catheter 110, and may use the signals to calculate position, orientation, distance, temperature and/or electrocardiogram (ECG) values for a distal tip in distal end 114. In an implementation, processing device(s) 140 may include a controller unit 144 for sending instructions to other devices in medical system 100. In an implementation, processing device(s) 202 may include a pacing signal unit 146 (e.g., implemented in hardware as processing circuits and/or software as a software module) and capture unit 148. Pacing signal unit 146 is configured to sequentially pace through each pair of microelectrodes 190, where pacing is the generation and delivery of a pace signal via a pair of microelectrodes 190. Capture unit 148 is configured to determine if a capture occurred in response to the pace signal, where a capture occurs if the pace signal was sent through living tissue as opposed to an ablated lesion. For example, catheter 110 can include an electrode 130 which is configured to capture an intracardiac signal responsive to the pace signal. In an implementation, an operator, e.g., a surgeon can see the capture on a display or sensor, for example. In an implementation, medical system 100 can determine gaps based on the captured signal. Further detail is provided herein below with respect to FIGS. 4-6. Processing units 142, 144, 146 and 148 are examples, and do not comprise all the possible functions that may be implemented in processing device(s) 140. Other functionality and/or processing units may be included in processing device(s) 140 but are not shown.

In the example of FIG. 1, console 120 can also be connected by a cable 150 to external sensors 152. External sensors 152 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic location sensors to locate catheter 110 during use. Although not shown in FIG. 1, external sensors 152 can be embedded in a vest that is configured to be worn by patient 102. External sensors 152 can aid in identifying and tracking the respiration cycle of patient 103. External sensors 152 can transmit information to console 120 via cable 150.

Additionally, or alternatively, catheter 110, and external sensors 152 can communicate with console 120 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth®, acoustic or other transmissions.

Catheter 110 can be equipped with a wireless digital interface that can communicate with a corresponding input/output (I/O) interface 160 in console 120. Wireless digital interface and the I/O interface 160 can operate in accordance with any suitable wireless communication standard that is known in the art, such as IR, RF, Bluetooth, one of the IEEE 802.11 families of standards, or the HiperLAN standard. External sensors 152 can include one or more wireless sensor nodes integrated on a flexible substrate. The one or more wireless sensor nodes can include a wireless transmit/receive unit (WTRU) enabling local digital signal processing, a radio link, and a power supply such as miniaturized rechargeable battery.

Wireless digital interface and the I/O interface 160 can enable console 120 to interact with catheter 110 and external sensors 152. Based on the electrical impulses received from external sensors 152 and signals received from catheter 110 via wireless digital interface and the I/O interface 160 and other components of medical system 100, processing device(s) 140 can generate information 105 which can be shown on a display 170. Information 105, can include, but is not limited to, capture signals as described herein below.

During the diagnostic treatment, processing device(s) 140 can present information 105, and/or can store data in a memory 180. Memory 180 can include any suitable volatile and/or non-volatile memory, such as random access memory or a hard disk drive.

Catheter control unit 112 can be configured to be operated by an operator 130 to manipulate catheter 110, based on information 105, which is selectable using one or more input devices 185. Alternatively, medical system 100 can include a second operator that manipulates console 120 while operator 130 operates catheter control unit 112 to manipulate catheter 110 based on information 105. The second operator can also be provided with information 105. The mechanics of the construction and use of catheter control device 112 to move and position distal end 114 of catheter 110 is within the state of the art such as employed in the CARTO™ mapping system referenced above. For example, see also U.S. Pat. No. 6,690,963 which is incorporated herein by reference as if fully set forth.

Figure 2:
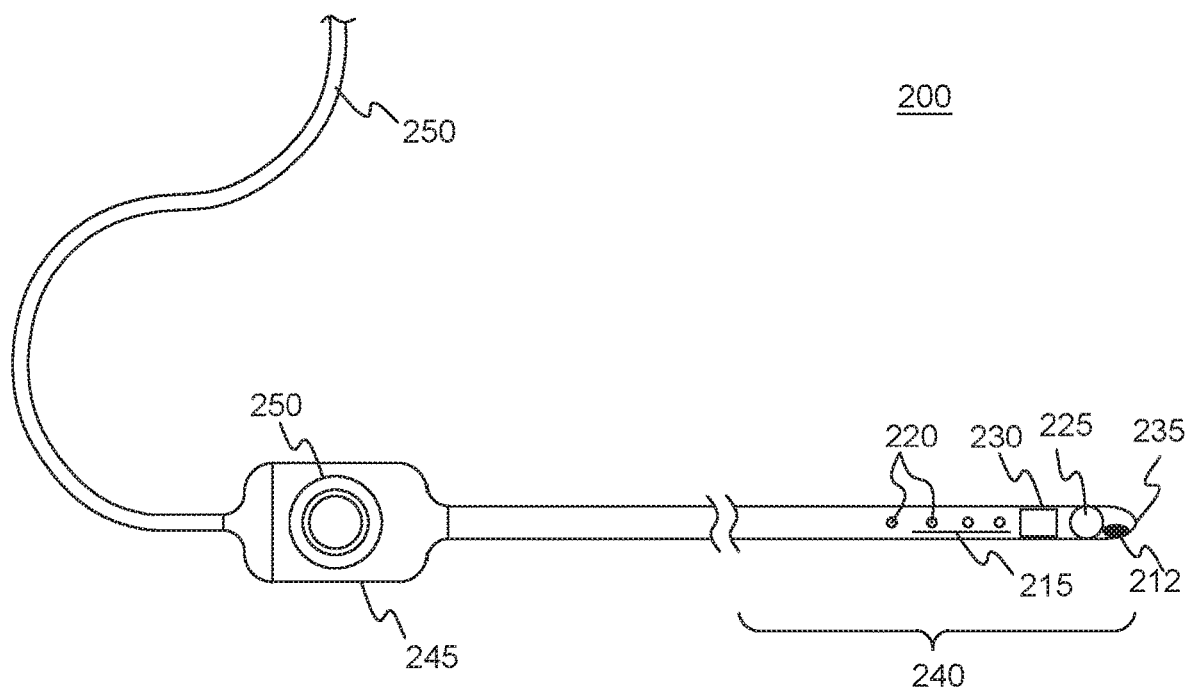
FIG. 2 is a schematic diagram of an example catheter in accordance with certain implementations.

An example catheter 200 is shown in greater detail in FIG. 2, showing some, but not all, of the elements that may be included in catheter 200. A catheter 200 may include, but is not limited to include, any one or more of the following components: electrode(s) 210; microelectrodes 212; temperature sensor(s) 215; non-contact electrodes 220; image sensor(s) 225; positioning or location sensor(s) 230; distal tip 235; distal end 240; handle 245; and/or cable 250. The schematic diagram of catheter 200 in FIG. 2 is a high-level representation of possible components of catheter 200, such that the location and configuration of the components in catheter 200 may be different than shown.

Distal end 240 of catheter 200 may include an electrode(s) 210 at distal tip 235 that may be used to measure electrical properties of the cardiac tissue. Electrode(s) 210 may also be used to send electrical signals to the heart for diagnostic purposes. Electrode(s) 210 may also perform ablation on defective cardiac tissue by applying energy (e.g., RF energy) directly to the cardiac tissue at the desired location of ablation.

Distal end 240 of catheter 200 may include microelectrode 212 at distal tip 235 that may be used to detect a gap in an ablation line. In an implementation, catheter 200 includes an electrode(s) 210 configured for ablation and microelectrodes 212 configured for gap detection.

Distal end 240 of catheter 200 may include temperature sensor(s) 215 to measure the temperature of the cardiac tissue in contact with distal end 240 and/or measure the temperature of distal end 240 itself. For example, thermocouples or thermistors for measuring temperature may be placed anywhere along distal end 240 to serve as temperature sensor(s) 215.

Distal end 240 may include non-contact electrodes 220 arranged in an array, which may be used to simultaneously receive and measure far-field electrical signals from the walls of the heart chamber of a patient. Electrode(s) 210, microelectrodes 212 and non-contact electrodes 220 provide information regarding the electrical properties of the heart to processing device(s) for processing, such as for example, processing device(s) 140.

Catheter(s) 200 may be equipped with one or more image sensor(s) 225, such as a charge coupled device (CCD) image sensor, and/or a camera for capturing endoscopic images when inserted in a body cavity. Image sensor(s) 225 may be located at distal end 240.

Distal end 240 may include location sensor(s) 230 in distal tip 235 of catheter 200 that may generate signals used to determine the position and orientation (and/or distance) of catheter 200 in the body. In an example, the relative position and orientation of location sensor(s) 230, electrode(s) 210, microelectrodes 212 and distal tip 235 are fixed and known in order to facilitate accurate positioning information of distal tip 235. For example, the position of location sensor(s) 230 may be determined in part based on the relative position to known positions outside the heart (e.g., based on extra-cardiac sensors). The use of location sensor(s) 230 may provide improved location accuracy within the magnetic fields in the surrounding space and provide location information that is adaptable to patient movement because the position information of catheter 200 is relative to the anatomy of the patient.

Handle 245 of catheter 220 may be operated by an operator such as a physician and may include controls 250 to enable the physician to effectively steer distal tip 235 in the desired direction.

Electrodes 210, microelectrodes 212, non-contact electrodes 220, and sensors 215, 225, 230 may be connected to processing device(s) 140 via wires that may pass through handle 245 and cable 250, in order to provide information, such as location, electrical, imaging and/or temperature information, to a console system, such as console 120, which may be used to operate and display the function of catheter 200 within the heart in real-time.

Figure 3:
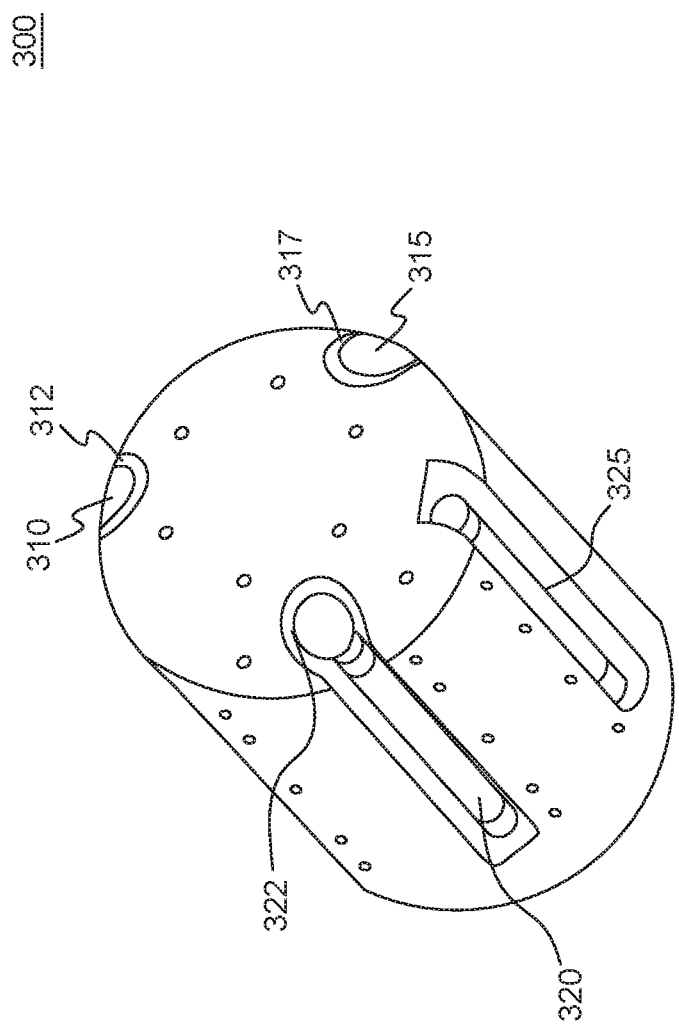
FIG. 3 is a diagram of an example distal tip of a catheter with microelectrodes in accordance with certain implementations.

FIG. 3 is a diagram of an example distal tip of a catheter 300 with microelectrodes in accordance with certain implementations. In an implementation, catheter 300 has a distal tip 305 that includes a set of three microelectrodes 310, 315 and 320. Each microelectrode 310, 315 and 320 can be made from, but is not limited to, a medical grade metal, such as palladium, platinum, gold, stainless steel and the like, and combinations thereof. Each microelectrode 310, 315 and 320 is set in a recess 312, 317 and 322 in distal tip 305 such that an outer surface of microelectrodes 310, 315 and 320 are flush with a contour of distal tip 305. In an implementation, microelectrodes 310, 315 and 320 are substantially evenly distributed around a circumference of distal tip 305. In an implementation, distal tip 305 can include a thermocouple(s) 325 to measure temperature, which in turn can be used to determine if and which pair of the microelectrodes 310, 315 and 320 are in contact the tissue.

Figure 4:
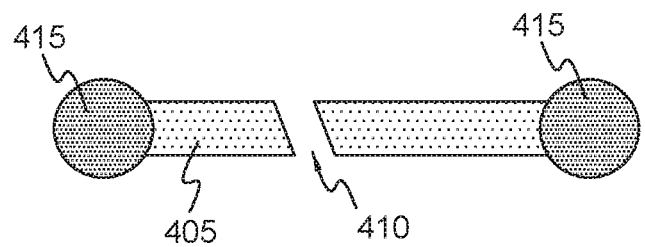
FIG. 4 is a flowchart for gap detection in accordance with certain implementations.

FIG. 4 shows an illustrative scenario 400 of where a method for gap detection can be used. Scenario 400 illustrates an ablation line 405 which includes a gap 410. A pair of microelectrodes 415 are shown that are in contact with ablation line 405 to try to detect gap 410 as described herein below with respect to FIG. 6.

Figure 5:
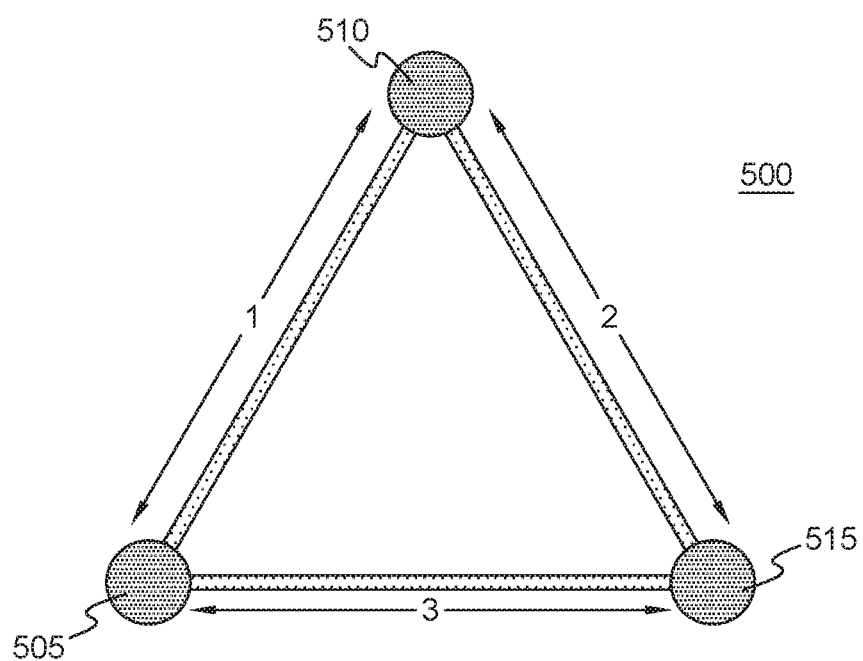
FIG. 5 is a schematic diagram of an ablation line using the method and system described herein in accordance with certain implementations.

FIG. 5 shows a pacing protocol 500 for a set of microelectrodes 505, 510 and 515 in accordance with certain implementations. Pacing protocol 500 sequences pacing signals from one pair of microelectrodes to another pair of microelectrodes for a given tissue location. For example, pacing protocol 500 can send a first pacing signal for microelectrodes 505 and 510, a second pacing signal for microelectrodes 510 and 515, and a third pacing signal for microelectrodes 515 and 505. Consequently, pacing protocol 500 and set of microelectrodes 505, 510 and 515 enable three readings for each tissue location. Pacing protocol 500 can be implemented, for example, in pacing signal unit 146.

In an implementation, pacing protocol 500 selects a particular pair of microelectrodes based on which pair(s) of microelectrodes is in contact with the target tissue. In an implementation, the operator and/or physician can know, by looking at the signals from each pair of microelectrodes, which pair(s) of microelectrodes is in contact with the tissue. For example, if there are no signals between a pair of microelectrodes, then there is no need to pace in that tissue location. The lack if signals, i.e., there is no energy, indicates that the pair of microelectrodes is not in contact with the tissue. This helps physicians during an ablation procedure if a gap is detected by a pair of microelectrodes, (which are by definition in contact with the target tissue), since the ablation electrode will also be in contact with the target tissue. That is, the place where pacing occurs is also the same place where ablation occurs. This is in contrast to prior systems where the place for pacing is not the same place for ablation. Moreover, the time of ablation is reduced since the pacing location is the same as the ablation location.

In an implementation, pacing protocol 500 can be automated by using contact force information to automatically detect the pair of microelectrodes that are in contact with the tissue. For example, force sensor 128 of FIG. 1 can be used to provide information to pacing signal unit 146 to automatically start pacing protocol at a particular pair of microelectrodes. In an implementation, force information can be used to omit a particular pair of microelectrodes.

Figure 6:
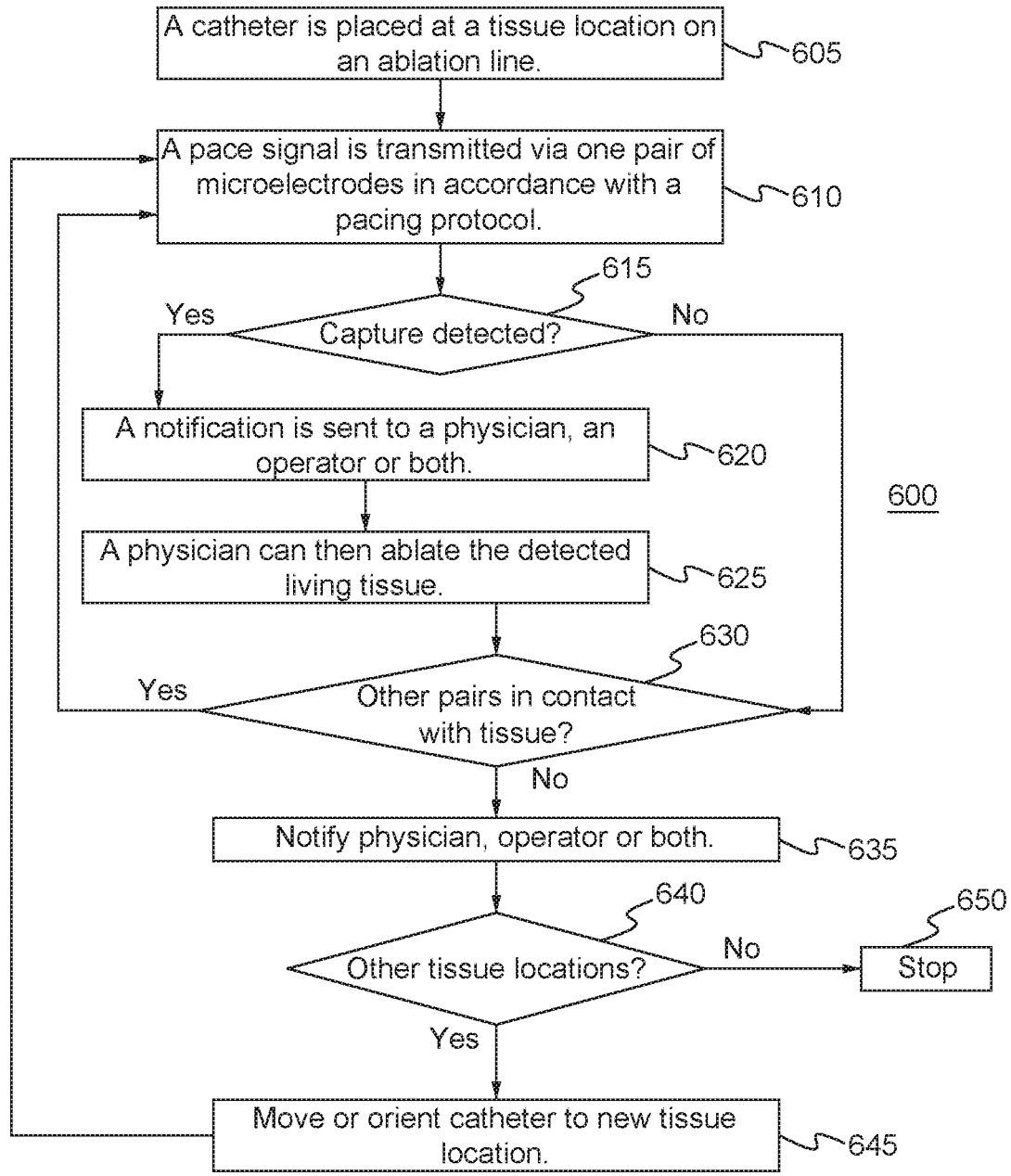
FIG. 6 is a schematic diagram of microelectrodes using a pacing sequence in accordance with certain implementations.
Figure 1:
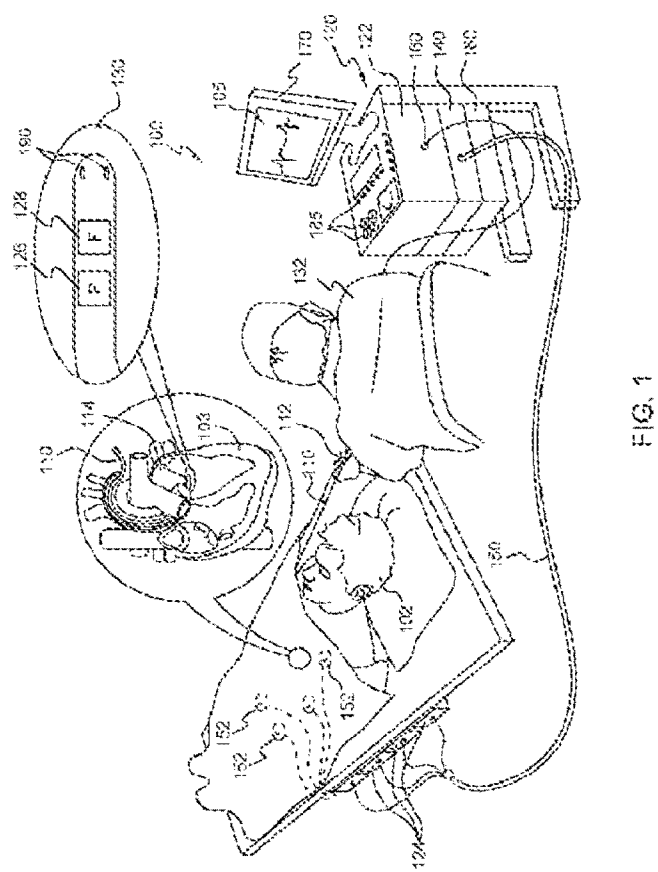
Figure 1A:
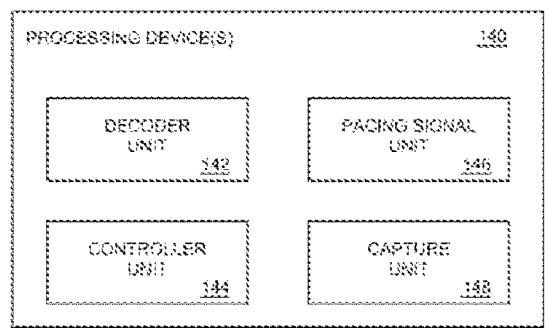
Figure 2:
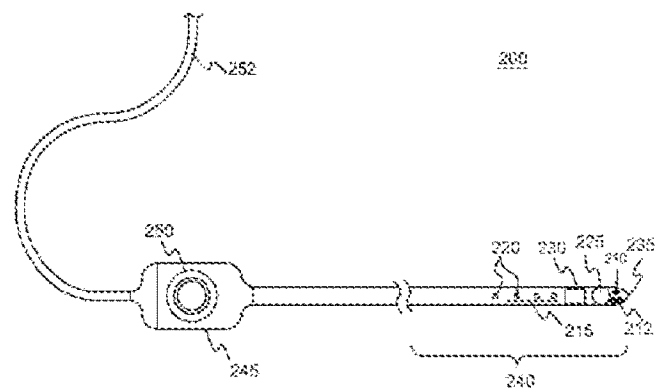

FIG. 6 is a flowchart 600 of a method for gap detection in accordance with certain implementations. Flowchart 600 is described in conjunction with FIG. 4 and FIG. 5. A catheter is placed at a tissue location on an ablation line, such as ablation line 405 (605). A pace signal is transmitted via one pair of microelectrodes in accordance with a pacing protocol, such as for example, pacing protocol 500 (610). For example, the pair of microelectrodes can be pair of microelectrodes 415 in FIG. 4 or one of the pair of microelectrodes formed from microelectrodes 505, 510 and 515 in FIG. 5. The system then determines if a capture has occurred (615). If no capture is detected, a determination is made at the current location as to whether other pairs of microelectrodes are in contact with the tissue (630). If a capture has been detected, a notification is sent to a physician, an operator or both that a gap exists in the ablation line (620). This is shown for example in FIG. 4, where a gap 410 has been detected in ablation line 405 by pair of microelectrodes 415. A physician can then ablate the detected living tissue (625). A determination is made at the current location as to whether other pairs of microelectrodes are in contact with the tissue (630). If another pair of microelectrodes is in contact with the tissue, a pace signal is transmitted via the pair of microelectrodes in accordance with a pacing protocol (610). If no other pairs of microelectrodes are in contact with the tissue, then notify physician and/or operator (635). Determine if there are other tissue locations that need to be checked (640). If more locations are available, then the catheter is moved or oriented for a new tissue location (645) and a pace signal is transmitted via one pair of microelectrodes in accordance with a pacing protocol, such as for example, pacing protocol 500 (610). If there are no more locations, then stop (650).

In general, a method for gap detection in an ablation line includes placing a catheter along the ablation line at a tissue location, transmitting a pacing signal via a pair of microelectrodes in accordance with a pacing protocol, receiving a capture signal if living tissue is present, determining a gap in the ablation line based on the capture signal and ablating the living tissue in the detected gap in the ablation line with an ablation electrode without catheter movement. In an implementation, the method further includes determining which pairs of microelectrodes are in contact with a target tissue in accordance with the pacing protocol. In an implementation, the method further includes using a force sensor to automatically detect which pairs of microelectrodes at the tissue location are in contact with the target tissue in accordance with the pacing protocol. In an implementation, the method further includes using a thermocouple to automatically detect which pairs of microelectrodes at the tissue location are in contact with the target tissue in accordance with the pacing protocol. In an implementation, the method further includes transmitting another pacing signal via another pair of microelectrodes at the tissue location without moving the catheter in accordance with the pacing protocol. In an implementation, the method further includes placing the catheter at another tissue location after sequencing through each pair of microelectrodes at the tissue location without moving the catheter in accordance with the pacing protocol. In an implementation, the method further includes using signaling between pairs of microelectrodes at the tissue location to determine if the catheter is in contact with the target tissue. In an implementation, the method further includes displaying the capture signal to a user.

In general, a system for gap detection in an ablation line includes a catheter including a plurality of microelectrodes and an ablation electrode, the catheter configured for placement along the ablation line at a tissue location and a processing device in communication with the plurality of microelectrodes and the ablation electrode. The processing device is configured to transmit a pacing signal via a pair of microelectrodes in accordance with a pacing protocol, receive a capture signal via an electrode if living tissue is present, determine a gap in the ablation line based on a received capture signal and cause ablation of the living tissue in a detected gap in the ablation line with the ablation electrode without movement of the catheter. In an implementation, the processing device further includes a pacing signal unit configured to determine which pairs of microelectrodes from the plurality of microelectrodes are in contact with a target tissue, and implement the pacing protocol based on the pairs of microelectrodes in contact with the target tissue. In an implementation, the system further includes a force sensor in communication with the pacing signal unit, the force sensor automatically detects which pairs of microelectrodes at the tissue location are in contact with the target tissue. In an implementation, the system further includes a thermocouple in communication with the pacing signal unit, the thermocouple detects which pairs of microelectrodes at the tissue location are in contact with the target tissue. In an implementation, the processing device is further configured to transmit another pacing signal via another pair of microelectrodes at the tissue location without moving the catheter in accordance with the pacing protocol. In an implementation, the processing device is further configured to use signals between pairs of microelectrodes at the tissue location to determine if the catheter is in contact with a target tissue. In an implementation, the system further includes a display for displaying the capture signal to a user.

In general, a catheter for use in gap detection along an ablation line of a target tissue includes a plurality of microelectrodes, wherein each pair of electrodes in contact with the target tissue transmits a pacing signal and an ablation electrode. The ablation electrode ablates living tissue in a gap in the ablation line detected from a capture signal from the target tissue responsive to the pacing signal, where transmission of the pacing signal and ablation are done with singular placement of the catheter at the target tissue. In an implementation, the catheter further includes a force sensor configured to automatically detect which pairs of microelectrodes are in contact with the target tissue. In an implementation, the catheter further includes a thermocouple configured to detect which pairs of microelectrodes are in contact with the target tissue. In an implementation, the plurality of microelectrodes and the ablation electrode are in a distal end of the catheter. In an implementation, the plurality of microelectrodes are in a recess and flush with an exterior surface of the catheter.

The description herein is with respect to cardiac ablation procedures for a cardiac system, although it is understood by one skilled in the art that the disclosures may be applied to systems and procedures that can be used in any cavity or system in the body, including, but not limited to, the respiratory/pulmonary system, the respiratory and pulmonary system, the digestive system, the neurovascular system, and/or the circulatory system.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for gap detection in an ablation line using a catheter comprising a tip including a plurality of microelectrodes configured to deliver a bipolar pacing signal to tissue and an impedance transducer configured to detect a capture signal, the method comprising:
    in a first placement of the catheter, placing the catheter along the ablation line at a first tissue location;
    in the first placement, transmitting a first pacing signal between a first two of the plurality of microelectrodes, to deliver the first pacing signal to tissue at the first tissue location;
    in the first placement, receiving a first capture signal from the impedance transducer if the first pacing signal pulses the heart;
    in the first placement, transmitting a second pacing signal between a second two of the plurality of microelectrodes to deliver the second pacing signal to tissue at the first tissue location;
    in the first placement, receiving a second capture signal from the impedance transducer if the second pacing signal pulses the heart; and
    in the first placement, if the first capture signal is received, ablating the tissue at the first tissue location with the impedance transducer;
    in the first placement, if the second capture signal is received, ablating the tissue at the first tissue location with the impedance transducer.

2. The method of claim 1, further comprising:
    determining which of the plurality of microelectrodes is in contact with tissue at the first tissue location.

3. The method of claim 2, wherein determining is performed using a force sensor to automatically detect which of the microelectrodes is in contact with tissue at the first tissue location.

4. The method of claim 2, wherein determining is performed using a thermocouple to automatically detect which of the plurality of microelectrodes is in contact with tissue at the first tissue location.

5. The method of claim 2, further comprising:
    transmitting a third pacing signal between a third two of the plurality of microelectrodes at the first tissue location without moving the catheter away from the first tissue location.

6. The method of claim 5, further comprising:
    placing the catheter at a second tissue location if no two of the plurality of microelectrodes is in contact with tissue at the first tissue location.

7. The method of claim 2, further comprising:
    using signaling between the microelectrodes to determine if the catheter is in contact with tissue at the first tissue location.

8. The method of claim 1, further comprising: upon receiving a capture signal from the impedance transducer, displaying an indication of the capture signal to a user.

9. A system for gap detection in an ablation line, comprising:
    a catheter including a plurality of microelectrodes and an impedance transducer, the catheter configured for a first placement along the ablation line at a first tissue location;
    a processing device in communication with the plurality of microelectrodes and the impedance transducer, the processing device configured to:
        in the first placement, transmit a first bipolar pacing signal between a first two of the plurality of microelectrodes;
        in the first placement, receive a first capture signal via the impedance transducer if the first pacing signal pulses the heart;

in the first placement, transmit a second bipolar pacing signal between a second two of the plurality of microelectrodes to deliver the second pacing signal to tissue at the first tissue location; and in the first placement, receive a second capture signal if the second pacing signal pulses the heart;

in the first placement, if the first capture signal is received, cause the impedance transducer to ablate tissue at the first tissue location, and in the first placement, if the second capture signal is received, cause the impedance transducer to ablate tissue at the first location.

10. The system of claim 9, wherein the processing device further comprises:

a pacing signal unit configured to:

in the first placement, determine which of the plurality of microelectrodes is in contact with tissue at the first tissue location; and in the first placement, implement a pacing protocol comprising transmitting a sequence of successive respective pacing signals between corresponding successive, respective pairs of the plurality of microelectrodes in contact with tissue at the first tissue location, and for each successive respective pair in the sequence, determining whether or not a corresponding capture signal is received from the impedance transducer, thereby testing for presence of living tissue at the first tissue location.

11. The system of claim 10, further comprising: a force sensor in communication with the pacing signal unit, the force sensor configured to automatically detect which of the plurality of microelectrodes is in contact with tissue at the first tissue location.

12. The system of claim 10, further comprising:

a thermocouple in communication with the pacing signal unit, the thermocouple configured to detect which of the plurality of microelectrodes is in contact with tissue at the first tissue location.

13. The system of claim 10, wherein the processing device is further configured to transmit a third pacing signal via a third two of the plurality of microelectrodes to deliver the third pacing signal to tissue at the first tissue location.

14. The system of claim 9, wherein the processing device is further configured to use signals between the microelectrodes to determine which of the plurality of microelectrodes is in contact with the tissue at the first tissue location.

15. The system of claim 9, further comprising: a display for displaying the capture signal to a user.

16. A catheter for use in gap detection and configured for a first placement along an ablation line at a first tissue location, the catheter comprising:

an impedance transducer disposed at a distal tip of the catheter;

a plurality of microelectrodes positioned about the distal tip of the catheter;

wherein a first two of the plurality of microelectrodes is configured to deliver a first bipolar pacing signal to tissue at the first tissue location in the first placement, such that in the first placement the impedance transducer detects a capture signal if the first pacing signal pulses the heart, and if the first pacing signal does not pulse the heart, the impedance transducer does not detect a capture signal;

wherein a second two of the plurality of microelectrodes is configured to deliver second bipolar pacing signal to tissue at the first tissue location in the first placement, such that the impedance transducer detects a capture signal in the first placement if the second pacing signal pulses the heart, and if the second pacing signal does not pulse the heart the impedance transducer does not detect a capture signal;

thereby determining a location for ablation in the first placement;

and if the impedance transducer detects a capture signal while the catheter is at the first tissue location, the impedance transducer is configured to perform in the first placement, an ablation of tissue at the first tissue location;

wherein detection and ablation is performed with only one placement of the catheter between sending the first pacing signal and performing the ablation.

17. The catheter of claim 16, further comprising:

a force sensor configured to automatically detect which of the microelectrodes is in contact with tissue.

18. The catheter of claim 16, further comprising:

a thermocouple configured to detect which of the microelectrodes is in contact with the tissue.

19. The catheter of claim 16, wherein the plurality of microelectrodes and the impedance transducer are arranged at a circumference of a substantially circular tip at the distal end of the catheter.

20. The catheter of claim 16, wherein each of the plurality of microelectrodes is disposed in a corresponding recess and flush with a lateral surface of the tip.

* * * * *

UNITED STATES PATENT AND TRADEMARK OFFICE
CERTIFICATE OF CORRECTION

| | | |
|---|---|---|
| PATENT NO. | : 11,484,359 B2 | |
| APPLICATION NO. | : 15/799254 | |
| DATED | : November 1, 2022 | |
| INVENTOR(S) | : Dror Berman et al. | |

It is certified that error appears in the above-identified patent and that said Letters Patent is hereby corrected as shown below:

In the Drawings
In Figure 1, and on the title page, the illustrative figure, reference numeral 130 has been changed to reference numeral 132. (See attached Replacement Sheet)
In Figure 2, reference numeral 210 has been added, and reference numeral 250 has been changed to reference numeral 252. (See attached Replacement Sheet)

In the Specification
In Column 3, Line 7, delete "patient 103" and insert -- patient 102 --, therefor.
In Column 3, Line 8, delete "patient 103." and insert -- patient 102. --, therefor.
In Column 4, Line 32, delete "processing device(s) 202" and insert -- processing device(s) 140 --, therefor.
In Column 4, Line 66, delete "patient 103." and insert -- patient 102. --, therefor.
In Column 6, Line 48, delete "catheter 220" and insert -- catheter 200 --, therefor.
In Column 7, Line 36, delete "lack if" and insert -- lack of --, therefor.

In the Claims
In Column 10, Line 19, in Claim 1, delete "heart; and" and insert -- heart; --, therefor.
In Column 10, Line 22, in Claim 1, delete "transducer;" and insert -- transducer; and --, therefor.
In Column 11, Line 4, in Claim 9, delete "location; and" and insert -- location; --, therefor.
In Column 12, Line 18, in Claim 16, delete "deliver second" and insert -- deliver a second --, therefor.

Signed and Sealed this
Fifth Day of September, 2023

Katherine Kelly Vidal
*Director of the United States Patent and Trademark Office*